United States Patent [19]
Pope

[11] Patent Number: 4,876,881
[45] Date of Patent: Oct. 31, 1989

[54] METHOD AND APPARATUS FOR MEASURING SETTLING RATE, COMPACTION, AND CLARITY OF A LIQUID

[75] Inventor: Daniel F. Pope, Issaquah, Wash.

[73] Assignee: Mt. Fury Company, Issaquah, Wash.

[21] Appl. No.: 231,767

[22] Filed: Aug. 12, 1988

[51] Int. Cl.$^4$ ...................... G01N 15/04; G01N 15/06
[52] U.S. Cl. ........................................................ 73/53
[58] Field of Search .................. 73/53, 61.4; 210/96.1, 210/143

[56] References Cited

U.S. PATENT DOCUMENTS

| | | | |
|---|---|---|---|
| 3,869,903 | 3/1975 | Beach et al. | 73/61.4 |
| 4,194,391 | 3/1980 | Rosenberger | 73/61.4 |
| 4,313,340 | 2/1982 | Schniewind | 73/61.4 |
| 4,318,296 | 3/1982 | Parker et al. | 73/61.4 |

Primary Examiner—Michael J. Tokar
Assistant Examiner—Michele Simons
Attorney, Agent, or Firm—Seed & Berry

[57] ABSTRACT

An apparatus and method for continuously measuring the settling rate, compaction, and clarity of a liquid. A liquid sample containing suspended solids is pumped into the bottom of a reservoir, and clarified liquid is allowed to overflow the top of the reservoir. Settling rate is measured by adjusting the pumping speed to maintain the interface between the clarified and unclarified portions of the suspension at a constant level. The slowing of this measured settling rate as solids accumulate in the test chamber is used to determine the percent ultimate compaction. Clarity is measured by allowing a sample to settle completely in the test chambers, at intervals that are provided by the need to occasionally remove the accumulated solids from the test chamber.

8 Claims, 3 Drawing Sheets

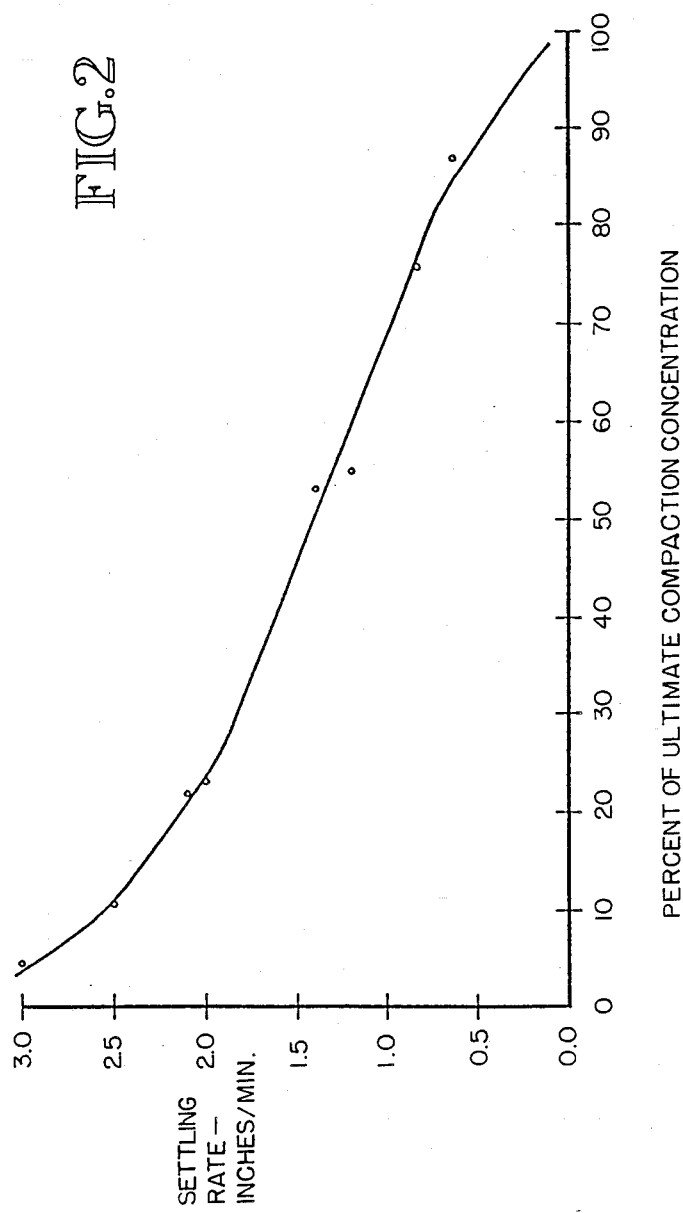

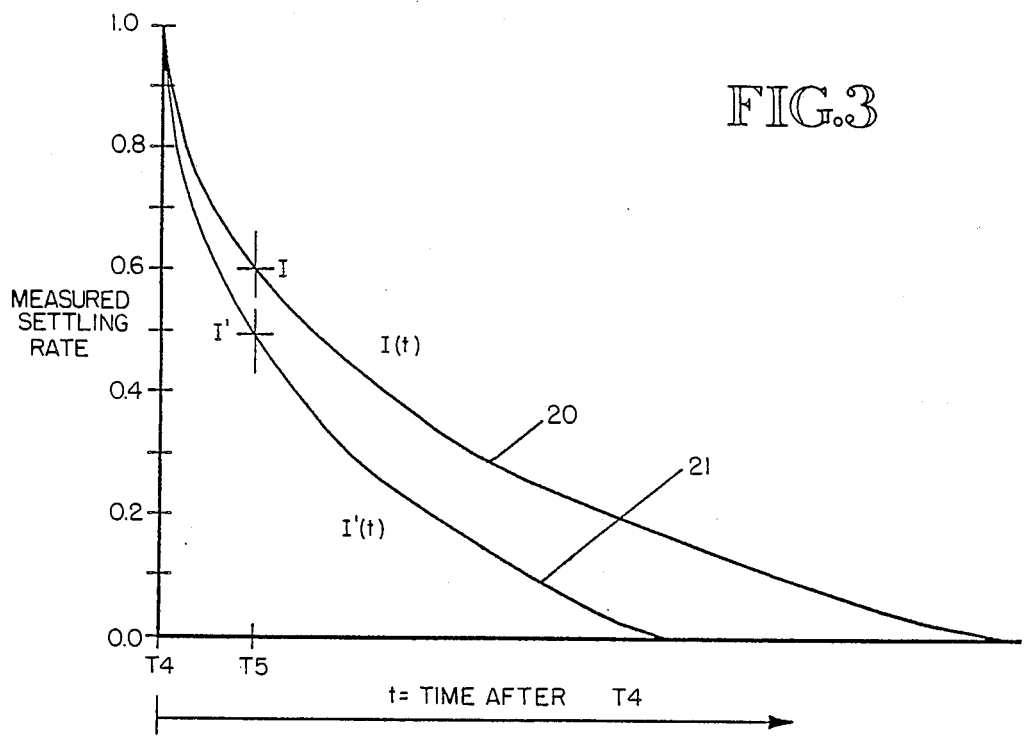

METHOD AND APPARATUS FOR MEASURING SETTLING RATE, COMPACTION, AND CLARITY OF A LIQUID

DESCRIPTION

1. Technical Field

The present invention relates to a method and an apparatus for testing solids in a liquid suspension for settling rate, compaction of the settled solids, and the resulting clarity of the liquid.

2. Background of the Invention

Settling rate has conventionally been measured by letting a liquid sample containing suspended solids sit in a container without agitation. As the solids settle, the surface clarifies first and the solids form an interface between the clarified and unclarified portions of the suspension. This interface falls at a given velocity, and this velocity defines the "settling rate." The settling rate will slow as solid concentration increases, and ultimate compaction is reached when the settling rate reaches zero.

When starting with a suspension of low concentration, settling will proceed until the solids reach their ultimate compaction. The settled solids then occupy a smaller percentage of the original suspension volume. This percentage is termed the "percent ultimate volume." Clarity of the fluid above the solid interface is indicative of the solids that have not settled and has been defined by conventional means.

Chemicals such as flocculents and coagulants are used to enhance this settling in that their action increases the efficiency of the accumulation of solids into flocs. As these chemicals are expensive or otherwise should not be used in excess, there is a need to adjust the chemical dosage to obtain the minimum acceptable settling rate.

The process of separating settled solids (or sludge) from clarified liquid is done commercially in equipment called "clarifiers" or "thickeners." In this equipment, sludge is pumped out from the bottom while clarified liquid is removed from the top. The operator of this equipment may control the sludge level by the rate of sludge removal and by the addition of flocculents or coagulants to the liquid suspension.

In order to adjust the chemical dosage necessary to obtain the minimum acceptable settling rate, an operator manually and intermittently must draw a sample from the suspension being added to the clarifier. This sample must then be tested to determine the settling rate, compaction of the settled solids, and resulting clarity. From these results, the operator can determine the appropriate dosage of flocculent or coagulant to be added to the clarifier.

Therefore, there is a need in the art for a more improved method and apparatus for measuring the settling rate, percent ultimate compaction, and clarity of a liquid containing suspended solids. Specifically, there is a need for an automatic and continuous method and apparatus for making these measurements. The present invention provides such a method and apparatus while further providing other related advantages.

SUMMARY OF THE INVENTION

Briefly stated, the present invention discloses a method and apparatus for continuously measuring over long periods of time the setting rate, compaction, and clarity of a liquid. A liquid sample containing suspended solids is pumped into the bottom of a reservoir, and clarified liquid is allowed to overflow the top of the reservoir. The settling rate is measured by adjusting the pumping speed to maintain the interface between the clarified and unclarified portions of the suspension at a constant level. The slowing of this measured settling rate as solids accumulate in the test chamber is used to determine the percent ultimate compaction. Clarity is measured by allowing a sample to settle completely in the test chamber, at intervals that are provided by the need to occasionally remove the accumulated solids from the test chamber.

BRIEF DESCRIPTION OF THE DRAWINGS

FIG. 2 shows the decrease in settling rate as the percent of ultimate compaction concentration increases.

FIG. 3 shows the decrease measured after time T4 of settling rates normalized to an actual settling rate of 1.0.

DETAILED DESCRIPTION OF THE INVENTION

Figure 1:
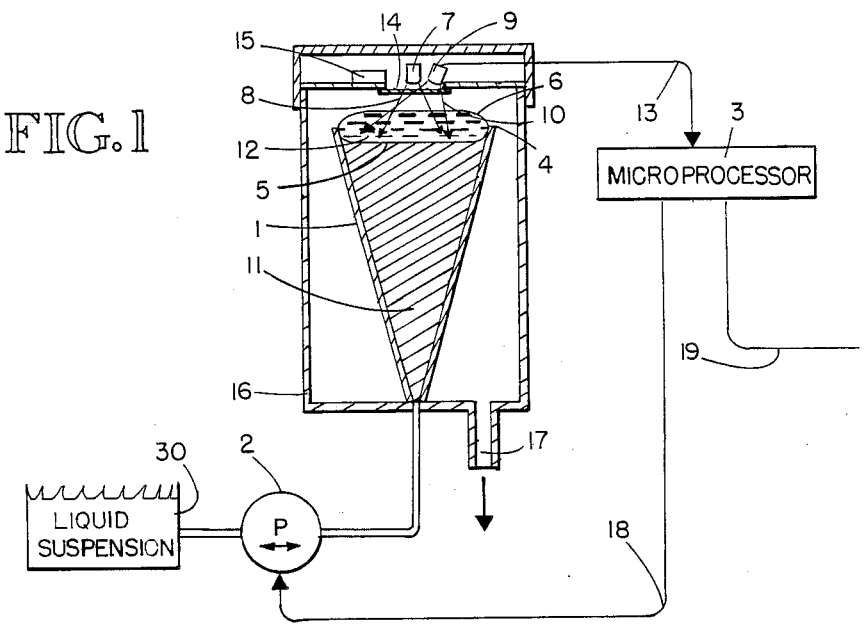
FIG. 1 is a side sectional view of an embodiment of the present invention.

Referring to FIG. 1, a liquid suspension 30 containing heavier-than-liquid solids is pumped into the bottom of reservoir 1 by pump 2. Pump 2 is a variable and reversible metering-type pump under the control of a microprocessor 3.

If the area of the open end 4 of reservoir 1 is A, and the volume per minute pumped into reservoir 1 is B, then the upwards velocity of the fluid going through area A is B/A. If the suspended solids 11 have a settling rate of C, then they will not descend if the pumping rate of pump 2 is adjusted such that:

$$C = B/A. \tag{1}$$

If the pumping rate is slower than this, an interface 5 between the clarified 12 and unclarified 11 portions of the suspension will form below the surface at some point where the horizontal area is smaller than A because of the taper of reservoir 1. While the conical shape of reservoir 1 is a useful embodiment of the present invention, the invention is not limited to any particular shape of reservoir. The reservoir need have only an inlet port near the bottom to allow the filling of the reservoir and permit overflow near the top.

An emitter 7 of focused light 8 and a scattered light detector 9 with, the focused field of view 10 are arranged such that a maximum sensitivity to unclarified solids 11 is obtained near the surface 6. As the suspension clarifies and the solids interface 5 drops, there is observed a decrease in the detector signal 13. A heater 15 is provided to maintain the window 14 above the temperature at which condensation or freezing would take place. Reservoir 1, emitter 7, and detector 9 may be surrounded by enclosure 16 to exclude light and to direct overflowing liquid to the drain 17.

The microprocessor 3 controls the pump 2 by means of a control signal 18 and reads the signal 13 from the detector 9 in a measurement cycle starting at time T0. At time T0, the pump 2 is run backwards sufficiently long to empty the reservoir 1. At time T1, the pump 2 is run forward sufficiently long to fill the reservoir 1 to overflowing. The pump 3 is then stopped from time T2 to T3 to allow sufficient settling to take place so that the detector signal 13 represents clarified water. This signal level, S0, is saved by the microprocessor 3 and may be calibrated in terms of conventional clarity scales. From time T3 to T4, the pump 2 is again run forwards to displace the settled solids 11 entirely from the reservoir 1, replacing them with new liquid suspension. At time T4, the detector signal 13 represents the signal produced by the unclarified suspension, and this signal level, S1, is saved by the microprocessor 3.

A set point, SP, for the detector signal 13 is then determined by the microprocessor 3 according to the formula:

$$SP = 0.4 \times S0 + 0.6 \times S1, \quad (2)$$

such that SP lies at 60% of the span between S0 and S1. The microprocessor 3 then controls the speed of the pump 2 to maintain the detector signal 13 at the set point, SP, using a conventional control algorithm, during the time interval between T4 and T5. For example, the microprocessor 3 speeds up the pump 2 if the detector signal 13 falls below SP, which raises the interface back to the desired level. By this means, the level of the interface 5 between the clarified and unclarified portions of the suspension can be maintained constant. Specifically, the relationship of the emitter 7, the detector 9, and the value of SP should be such that the solid interface 5 is located just deep enough that solids 11 are not swept over the rim 4 of the reservoir 1 and only clarified liquid 12 overflows. Therefore, the settling rate at a given moment can be determined from the pumping speed by formula (1). At time T5, the cycle repeats, starting again at T0 with the emptying of reservoir 1.

Referring to FIG. 2, the measured settling rate of solids drops as solid concentration increases. During the time interval from T4 to T5, solids will accumulate in the reservoir and thus the settling rate will decrease. This effect may then be used to determine the percent ultimate volume of the sample suspension.

Referring to FIG. 3, measured settling rates are shown normalized to an actual settling rate of 1.0. At time T4, the measured settling rate equals the actual settling rate. By time T5, the measured settling rate has decreased, as shown by curves 20 and 21, for two differing percent ultimate volumes.

Curve 20 defines a function of time, I(t), that relates to a percent ultimate volume V and has the value I(0) = 1 at T4 and value I at time T5. This may be approximated between T4 and T5 by the exponential function:

$$I(t) = EXP(-k \times t) \quad (3)$$

for some positive constant k determined empirically. I(t) may then be used to calculate the actual suspension settling rate from the measured settling rate by multiplying the measured settling rate by I(0)/I(t).

If the percent ultimate volume increases from V to V', then the measured settling rate will differ from I(t), as shown by curve 21. If we call this new function I'(t), relating to V' and having the value of I' at time T5, then a functional relationship exists between I, I', V and V'. This relationship may be approximated by the formula:

$$I - I' = K \times (V' - V) \quad (4)$$

for some positive constant K.

Those versed in the art can see that curves 20 and 21 may be determined numerically from the empirical curve of FIG. 2 by calculating the mass of solids pumped into the reservoir 11 up to time t. When enough suspension has been pumped in, the measured settling rate goes to zero. If the interval between T4 and T5 were long enough for this to happen, then the percent ultimate volume could be calculated directly from the volume V1 of suspension pumped into the volume V0 of the reservoir using the formula:

$$V = 100\% \times V0/V1. \quad (5)$$

Obviously, the use of formula (4) eliminates the need to wait as long as formula (5) requires to determine percent ultimate volume. Time T5 may conveniently be selected such that the measured settling rate decreases only about 40% between T4 and T5.

Referring again to FIG. 1, the determined values of settling rate, percent ultimate volume, and clarity may be displayed by the microprocessor 3 as signal 19 in any convenient manner. The settling rate measurement may then be used to control flocculent or coagulant dosages to equipment such as clarifiers or thickeners. For example, the settling rate set point, SP, used by the microprocessor 3 may be varied automatically in proportion to variations in the measured percent ultimate volume. Therefore, a higher percent ultimate volume (a less compact sludge) causes a higher settling rate set point, dosing more flocculent or coagulant into a clarifier. Similarly, varying the settling rate set point in inverse proportion to measured clarity variations changes clarity by removing more or less solids from suspension. The correction of compaction and clarity variations may be done by the microprocessor 3 using these or other means once the measurements have been made.

From the foregoing, it will be appreciated that although specific embodiments of the invention have been described herein for purposes of illustration, various modifications may be made without deviating from the spirit and scope of the invention. Accordingly, the invention is not limited except as by the appended claims.

I claim:

1. In a method for determining the settling rate and percent ultimate compaction of suspended solids in a liquid sample, of the type wherein a reservoir, having an inlet port near the bottom and which will permit overflow near the top, is filled with the liquid sample and the level within the reservoir of an interface formed between the clarified and unclarified portions of the liquid sample is measured, the improvement comprising:
   adjusting the rate at which additional sample is supplied to the reservoir through the inlet port so that the interface level is maintained at a desired constant level within the reservoir;
   calculating the settling rate from the necessary adjustments to the rate at which liquid sample is supplied to the reservoir; and
   calculating the percent ultimate compaction from the slowing of the settling rate as liquid sample is supplied to the reservoir.

2. An apparatus for determining a physical property of solids suspended in a liquid sample, comprising:
   a reservoir to contain the liquid sample, the reservoir having an inlet port near the bottom and which will permit overflow near the top;
   a pump for adjustably supplying the liquid sample to the reservoir through the inlet port at a rate sufficient to maintain an interface between a clarified portion and an unclarified portion of the liquid sample at a desired level within the reservoir;

a detector for measuring the level within the reservoir of the interface formed between the clarified and unclarified portions of the liquid sample;

a microprocessor for controlling the pump to adjust the rate of supply of the liquid sample to maintain the desired interface level in response to changes in the measured interface level, and for calculating the physical property of the suspended solids in response to the rate of supply by the pump of the liquid sample to the reservoir necessary to maintain the interface at the desired level; and an enclosure around the reservoir and the detector, the enclosure having an outlet port near the bottom to permit drainage, the enclosure serving to exclude light.

3. A method for determining a physical property of solids suspended in a liquid sample, comprising:

providing a reservoir to contain the liquid sample, the reservoir having an inlet port near the bottom and which will permit overflow near the top;

filling the reservoir through an inlet port near the bottom of the reservoir;

adjustably supplying the liquid sample to the reservoir through the inlet port at a rate sufficient to maintain an interface between a clarified portion and an unclarified portion of the liquid sample at a desired level within the reservoir;

measuring the level within the reservoir of the interface formed between the clarified and unclarified portions of the liquid sample;

controlling the rate of supply of the liquid sample to maintain the desired interface level in response to changes in the measured interface level;

calculating the settling rate of the solids suspended in the liquid sample in response to the rate of supply of the liquid sample to the reservoir necessary to maintain the interface at the desired level; and calculating the percent ultimate compaction from the slowing of the settling rate as liquid sample is supplied to the reservoir to maintain the interface at the desired level.

4. An apparatus for determining a physical property of solids suspended in a liquid sample, comprising:

a reservoir to contain the liquid sample, the reservoir having an inlet port near the bottom and which will permit overflow near the top;

supply means for adjustably supplying the liquid sample to the reservoir through the inlet port at a rate sufficient to maintain an interface between a clarified portion and an unclarified portion of the liquid sample at a desired level within the reservoir;

measuring means for measuring the level within the reservoir of the interface formed between the clarified and unclarified portions of the liquid sample, said measuring means comprising an emitter of focused light and a scattered light detector;

control means for controlling the supply means to adjust the rate of supply of the liquid sample to maintain the desired interface level in response to changes in the measured interface level;

means for calculating the physical property of the suspended solids in response to the rate of supply by the supply means of the liquid sample to the reservoir necessary to maintain the interface at the desired level; and an enclosure around the reservoir and the measuring means, the enclosure having an outlet port near the bottom to permit drainage, the enclosure serving to exclude light.

5. The apparatus of claim 4, wherein the reservoir is conical, the inlet port being located in the tapered end portion of the bottom of the conical reservoir, and the conical reservoir having an open top.

6. The apparatus of claim 4, wherein the supply means is a variable and reversible metering-type pump.

7. The apparatus of claim 4, wherein the control means is a microprocessor.

8. The apparatus of claim 4, wherein the means for calculating is a microprocessor.

* * * * *